United States Patent
Warner et al.

(10) Patent No.: US 11,913,822 B2
(45) Date of Patent: Feb. 27, 2024

(54) SYSTEMS AND METHODS FOR MEMBRANE BLOCKAGE DETECTION IN GAS DETECTORS

(71) Applicant: Carrier Corporation, Palm Beach Gardens, FL (US)

(72) Inventors: Tanner Warner, Chanhassen, MN (US); Jon K. Evju, Shakopee, MN (US)

(*) Notice: Subject to any disclaimer, the term of this patent is extended or adjusted under 35 U.S.C. 154(b) by 0 days.

(21) Appl. No.: 17/823,246

(22) Filed: Aug. 30, 2022

(65) Prior Publication Data
US 2023/0088247 A1 Mar. 23, 2023

Related U.S. Application Data
(60) Provisional application No. 63/261,492, filed on Sep. 22, 2021.

(51) Int. Cl.
*G01F 5/00* (2006.01)
(52) U.S. Cl.
CPC ..................... *G01F 5/00* (2013.01)
(58) Field of Classification Search
CPC .............. G01F 5/00; G01N 33/0009
See application file for complete search history.

(56) References Cited

U.S. PATENT DOCUMENTS

| | | | | |
|---|---|---|---|---|
| 7,413,645 | B2* | 8/2008 | Scheffler | G01N 33/0006 205/780.5 |
| 11,415,562 | B2* | 8/2022 | Sexton | G01N 29/024 |
| 2006/0157408 | A1* | 7/2006 | Kuroda | B01D 61/22 210/90 |
| 2016/0320361 | A1 | 11/2016 | Johansen et al. | |
| 2017/0227499 | A1* | 8/2017 | Miller | G01N 29/04 |
| 2020/0166495 | A1* | 5/2020 | Stokoe | G01N 29/222 |
| 2020/0363306 | A1* | 11/2020 | Sexton | G01N 29/449 |
| 2021/0199635 | A1 | 7/2021 | Stokoe et al. | |
| 2021/0348987 | A1* | 11/2021 | Moix Olive | G08B 17/107 |

OTHER PUBLICATIONS
EP Application No. 22195967.9, Search Report, dated Feb. 13, 2023, 8 pages.

* cited by examiner

*Primary Examiner* — Francis C Gray

(57) ABSTRACT

Methods and systems for detecting membrane blockage in a gas detector are disclosed. In some embodiments, the gas detector comprises a membrane defining a sensing chamber of the detector, the sensing chamber comprising a relaxed state pressure. The method comprises applying one or more forces on one or more walls of the membrane, wherein applying the force causes a volume change inside the sensing chamber. The method further comprises measuring a pressure change inside the sensing chamber, the pressure change being caused by the volume change. The method further comprises determining a rate of return to the relaxed state inside the chamber and determining a condition of the membrane based on the determined rate of return to the relaxed state.

20 Claims, 5 Drawing Sheets

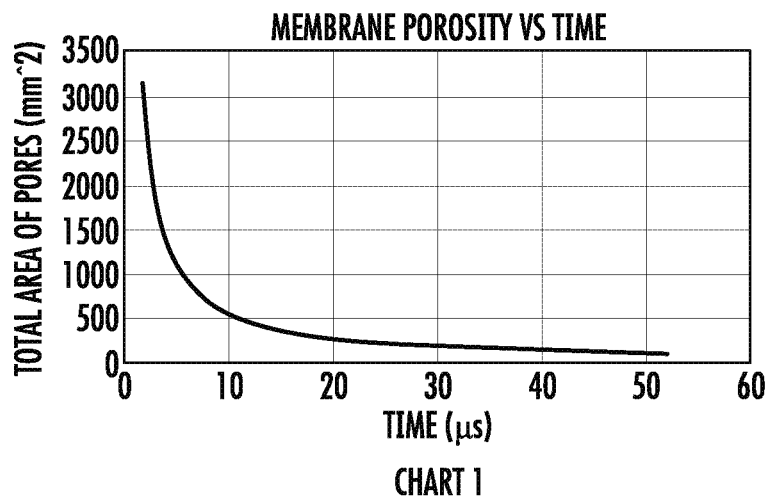
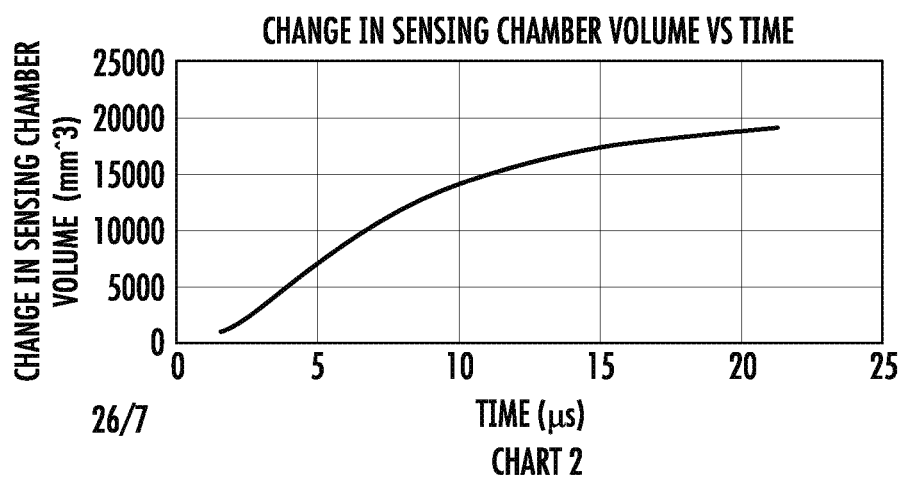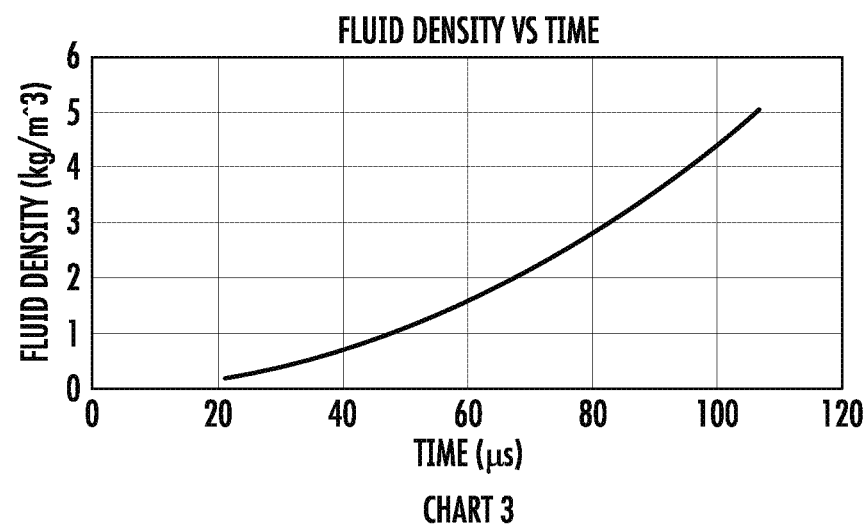
FIG. 1-A

SYSTEMS AND METHODS FOR MEMBRANE BLOCKAGE DETECTION IN GAS DETECTORS

CROSS REFERENCE TO A RELATED APPLICATION

The application claims the benefit of U.S. Provisional Application No. 63/261,492 filed Sep. 22, 2021, the contents of which are hereby incorporated in their entirety.

BACKGROUND

The invention relates generally to membrane blockage detection and, more specifically, to membrane blockage detection in gas detectors.

Gas detectors may generally use weather shields to protect sensors from the environment (e.g., water, dirt, debris, etc.). Some weather shields may include a hydrophobic membrane that allows gas to flow through while still blocking water. However, the hydrophobic membrane may become blocked or clogged with dust and debris, which may impede gas detection on gas detectors.

BRIEF DESCRIPTION

Aspects of the disclosure relate to methods, apparatuses, and/or systems for membrane blockage detection.

In some embodiments, a method for detecting membrane blockage in a gas detector is disclosed. In some embodiments, the gas detector comprises a membrane defining a sensing chamber of the detector, the sensing chamber comprising a relaxed state pressure. The method comprises applying one or more forces on one or more walls of the membrane, wherein applying the force causes a volume change inside the sensing chamber. The method further comprises measuring a pressure change inside the sensing chamber, the pressure change being caused by the volume change. The method further comprises determining a rate of return to the relaxed state inside the chamber and determining a condition of the membrane based on the determined rate of return to the relaxed state pressure.

In some embodiments, determining the rate of return to the relaxed state comprises determining an amount of time for the pressure inside the chamber to reach a fraction of a peak pressure change.

In some embodiments, the determined condition indicates presence of blockage in the membrane.

In some embodiments, the determined condition indicates whether the membrane is ruptured or missing.

In some embodiments, presence of blockage in the membrane is determined responsive to the determined rate of return to the relaxed state pressure being above a threshold rate of return.

In some embodiments the threshold rate of return is determined based on at least one of: porosity of the membrane, an amount of volume change, and type of gas inside the sensing chamber.

In some embodiments, the method further comprises determining an amount of blockage of the membrane based on the determined rate of return to the relaxed state pressure.

In some embodiments, the method further comprises determining a remaining operational life of the membrane based on the determined rate of return to the relaxed state pressure.

In some embodiments, the method further comprises sending an alert to a user, the alert indicating the condition of the membrane.

In some embodiments, the one or more forces may cause debris to fall off the membrane.

In some embodiments, a gas detector is provided. The gas detector comprises a membrane configured to define a sensing chamber of the gas detector, the sensing chamber comprising a related state pressure; a moving body operatively connected to one or more walls of the membrane, the moving body configured to apply one or more or more forces on the one or more walls of the membrane, wherein applying the force causes a volume change inside the sensing chamber; a pressure sensor configured for measuring pressure change inside the sensing chamber, the pressure change being caused by the volume change; and a controller operatively connected to the pressure sensor and the moving body, the controller configured to: determine a rate of return to the relaxed state inside the chamber; and determine a condition of the membrane based on the determined rate of return to the relaxed state pressure.

In some embodiments, the controller may be configured to determine an amount of blockage of the membrane based on the determined rate of return to the relaxed state pressure.

In some embodiments, the controller may be configured to determine a remaining operational life of the membrane based on the determined amount of blockage of the membrane.

In some embodiments, the moving body is an electroactive polymer.

In some embodiments, the electroactive polymer is embedded in the membrane.

In some embodiments, the gas detector comprises an actuator operatively coupled with the moving body and the controller, the actuator configured to cause the moving body to apply the force on the membrane.

In some embodiments, the controller is configured to send an alert to a user, the alert indicating the condition of the membrane.

Various other aspects, features, and advantages of the invention will be apparent through the detailed description of the invention and the drawings attached hereto. It is also to be understood that both the foregoing general description and the following detailed description are examples and not restrictive of the scope of the invention.

BRIEF DESCRIPTION OF THE DRAWINGS

FIG. 1-A shows example charts illustrating the operation of a gas detector, in accordance with one or more embodiments.

DETAILED DESCRIPTION

Figure 1:
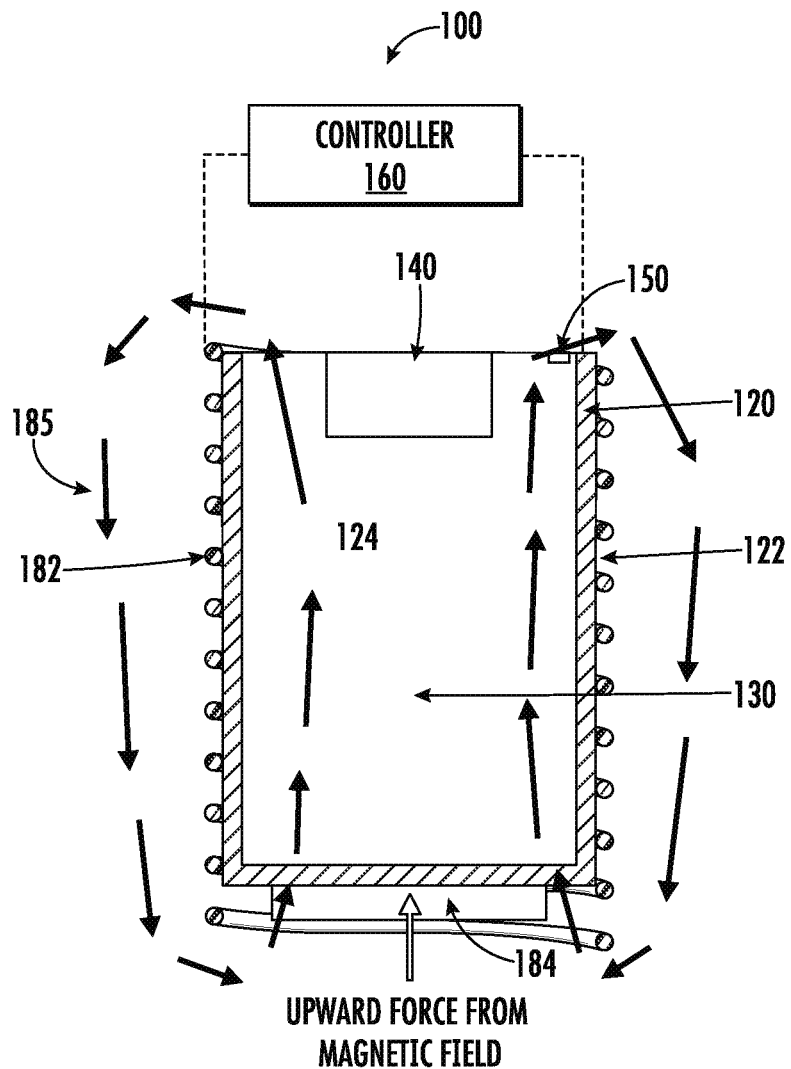
FIG. 1 is a perspective side view of an example of a gas detector, in accordance with one or more embodiments.

In the following description, for the purposes of explanation, numerous specific details are set forth in order to provide a thorough understanding of the embodiments of the invention. It will be appreciated, however, by those having skill in the art that the embodiments of the invention may be practiced without these specific details or with an equivalent arrangement. In other cases, well-known structures and devices are shown in block diagram form in order to avoid unnecessarily obscuring the embodiments of the invention.

The present disclosure, in accordance with some embodiments, describes methods and systems for detecting membrane blockage in gas detectors. In some embodiments, gas sensors may include a weather shield meant to protect the sensor interface of the gas sensor from the environment (e.g., water, dust, debris, etc.) that may affect the sensor performance. In some cases, weather shields may include a membrane that defines a sensing chamber where the gas sensing interface is located. The membrane may be configured to allow gas to flow through, but blocks liquids (e.g. water) from reaching the gas sensing interface. The membrane may get dirty or clogged which may prevent the gas from flowing into the sensing chamber and from reaching the gas sensing interface.

The present disclosure, in some embodiments, describes methods and systems for detecting membrane blockage. In some embodiments, membrane blockage may be detected by modifying the volume inside the sensing chamber and measuring the pressure change inside the chamber that results from the volume modification. In some embodiments, the volume inside the chamber may be modified by applying one or more forces to one or more walls of the membrane to increase or decrease the volume. The applied force may be one or more of mechanical, electrical, magnetic, acoustic, or other type of force that may cause the volume inside the chamber to change. In some embodiments, the applied force(s) may distort the membrane's shape which may cause the volume change inside the sensing chamber. In some embodiments, the applied force(s) may affect the volume inside the chamber by causing one or more walls of the membrane to contract, expand, flex, change shape, or move. Examples of methods and systems for generating such force are described hereinbelow.

In some embodiments, a change in volume inside the sensing chamber may affect the pressure inside the sensing chamber. In some embodiments, a volume decrease inside the chamber may cause the pressure to increase. Gas flowing through the membrane allows the pressure to equalize after a period of time. Similarly, a volume increase inside the chamber may cause the pressure to decrease. Gas flowing through the membrane allows the pressure to equalize after a period of time. In some embodiments, the pressure change results in a pressure peak relating to either the induced maximum or minimum pressure. In some embodiments, the sensing chamber may return to a relaxed state pressure. The rate of return to the relaxed state pressure may be indicative of whether the membrane is blocked. In some embodiments, the amount of time it takes the peak pressure inside the chamber to decay to a fraction of the peak pressure may be indicative of presence of blockage in the membrane. In some embodiments, this amount of time may be compared to an amount of time in a clean membrane to determine whether the membrane is blocked.

In some embodiments, the amount of time it takes the pressure to return to equilibrium (pressure before applying force) may be indicative of blockage. In some embodiments, the amount of time it takes the pressure to equalize may be indicative of blockage. For example, if there is no blockage, the pressure equalizes in a short amount of time (almost instantaneously). In the case of presence of a blockage, it may take longer for the pressure to equalize.

In some embodiments, applying one or more forces to the membrane may cause the membrane to move which in turn may cause the membrane to unclog (shake the debris off). For example, the membrane may unclog as a result of testing for blockage. In some embodiments, controller may conduct a second test after the first test to check if the membrane is unclogged (or if there is change in the amount of blockage as a result of the first testing). In some embodiments, the controller may apply a force in a serial manner (e.g., consecutively) or apply a strong force to shake off debris responsive to determining that the membrane is clogged. The stronger force may be part of a second test, or may be intended for cleaning, in which case, the controller may run another test after applying the stronger force to check for changes in the amount of blockage.

In some embodiments, cleaning the membrane using the pressure change caused by the applied force may be done independently of determining the condition of the membrane. In some embodiments, the pressure changing caused by the applied force(s) may be activated in a serial fashion in order to attempt to clear debris or blockage by vibration or movement of the membrane. For example, in a "cleaning" mode or a "preventive" mode, the controller may be configured to apply the force(s) periodically (e.g., on a schedule) as a form of preventive measure to prevent the membrane from clogging, and without going through the steps of determining whether the membrane is clogged. In some embodiments, the controller may test the membrane for blockage after the cleaning mode.

In some embodiments, the pressure change may be used as an indicator the membrane is ruptured, torn, or is missing, which can be used to warn the user and call for maintenance.

The methods and systems in the present disclosure may be beneficial because they use the sensing chamber itself in creating the volume change and in-turn the pressure change. This technology may allow users to remotely monitoring gas detectors to detect if the detector membrane is clean, or if it is becoming blocked, needing to be cleaned or changed out. With this advance warning, the end-user may schedule maintenance to clean or replace the hydrophobic membrane prior to failure and reduce costly down-time or gas detector failures due to blocked membranes.

FIG. 1 is a perspective side view of an example of a gas detector 100, in accordance with one or more embodiments. In some embodiments, gas detector 100 may include a membrane 120, a gas sensing interface 140, and a pressure sensor 150. In some embodiments, gas detector 100 may include a controller 160 operatively connected to one or more components of gas detector 100. In some embodiments, controller 160 may be configured to control one or more operations of gas detector 100. In some embodiments, controller 160 may include one or more processors configured to execute instructions stored on a memory to perform one or more operations of gas detector 100 described herein. Other components known to one of ordinary skill in the art may be included in controller 160 or in gas detector 100 to gather, process, transmit, receive, acquire, and provide information used in conjunction with the disclosed embodiments.

In some embodiments, membrane 120 may be configured to form a sensing chamber 130 where gas sensing interface 140 is located. In some embodiments, membrane 120 may be a porous membrane, that acts as a barrier, and configured to allow gas to flow into sensing chamber 130 and reach gas sensing interface 140 while filtering out other elements (e.g., liquids, dust, debris, etc.). The permeability (number and size of the pores) of membrane 120 may depend on type of gas the gas detector 100 is configured to detect (e.g., different membranes with different permeabilities may be used in different gas detectors, depending on the gas to be detected). In some embodiments, membrane 120 may be a hydrophobic membrane configured to repel and prevent liquids (e.g., water) from reaching sensing chamber 130. In some embodiments, membrane 120 may be flexible. For example, membrane 120 may expand, flex, or change shape. In some embodiments, a force may be applied on one or more of the membrane walls to cause the volume change inside the chamber (e.g., by causing one or more walls of the membrane to contract, expand, flex, change shape, or move). In some embodiments, the volume change inside the sensing chamber may be at least 0.75% of the volume. In some embodiments, the volume change may be at least between 0.75% and 3% of the volume. In some embodiments, the volume change may be at least between 0.75% and 5% of the volume.

In the example shown in FIG. 1, a solenoid 180 is used to generate a force on membrane 120. In some embodiments, solenoid 180 may include a coil 182 and magnet 184. In some embodiments, coil 182 is placed on outer wall 122 of membrane 120 outside of chamber 130. For example, coil 182 may surround some or all of membrane 120. In some embodiments, coil 182 may be placed inside the sensing chamber and may be operatively connected to or proximate to inner wall 124 of membrane 120. Magnet 184 may be operatively connected to an outer wall or an inner wall of membrane 120. In some embodiments, coil 182 may be configured to be operatively connected to controller 160. In some embodiments, solenoid 180 may be actuated by sending an electric current through coil 182 (e.g., by controller 160). A magnetic field may be created as shown by arrows 185, moving a magnet 184 upward in the direction of arrows 185. As a result, magnet 184 pushes on the membrane 120, changing the volume in chamber 130 temporarily.

In some embodiments, duration of the actuation of the solenoid may be determined based on the desired volume change. Controller 160 may be configured to determine the duration of the actuation based on the desired volume change, type of membrane, or type of gas sensor. In some embodiments, controller 160 may be configured to stop the solenoid actuation responsive to the volume change reaching a predetermined value. The predetermined value of volume change may be set by a user or determined by controller 160. For example, in some embodiments, the amount of volume change may be based on one or more of type of membrane, type of gas sensor, or previous tests. For example, controller 160 may be configured to adjust the amount of volume change based on times or results of previous tests.

Pressure sensor 150 may be configured to measure pressure changes inside the sensing chamber. For example, pressure sensor 150 may measure the pressure change inside chamber 130 caused by the volume change (decrease or increase). In some embodiments, pressure sensor 150 may be configured to measure the pressure inside the chamber continuously, periodically, or on demand. In some embodiments, controller 160 may be configured to control operations of pressure sensor 150 (e.g., turn ON/OFF) based on changes in the volume inside the chamber. For example, controller 160 may be configured to turn on the pressure sensor 150 at the time of actuating solenoid 180 (e.g., just before, at the same time or just after actuating the solenoid). In some embodiments, controller 160 may be configured to turn pressure sensor OFF in response to the pressure inside the chamber returning to a relaxed state pressure, equalizing, and/or reaching a fraction of a peak pressure change.

In some embodiments, pressure inside sensing chamber 130 may equalize after a period of time as a result of gas flowing through membrane 120 (e.g., in or out of membrane 120). A rate of return to a relaxed state pressure may indicate the condition of membrane 120. In some embodiments, controller 160 may be configured to determine a rate of return to the relaxed state pressure inside the chamber. In some embodiments, determining the rate of return to the relaxed state pressure may include determining an amount of time for the pressure inside the chamber to reach a fraction of a peak pressure change. In some embodiments, the rate of return to the relaxed state may include determining the period of time it takes the pressure to return to the equilibrium pressure (pressure before applying the force).

In some embodiments, controller 160 may be configured to determine a condition of the membrane based on the determined rate of return to the relaxed state pressure. For example, controller 160 may be configured to determine presence of blockage in the membrane responsive to the determined rate of return to the relaxed state pressure reaching (or being above) a threshold rate of return. For example, in absence of the blockage, the return to the relaxed state pressure is almost instantaneous. Similarly, controller 160 may determine the condition of the membrane 120 based on the amount of time it takes the pressure to reach a pre-determined fraction of the peak pressure. For example, if there is no blockage, the pressure may reach a fraction of the peak in a short amount of time (almost instantaneously). In some embodiments, if the membrane is clogged less gas may be able to flow through the membrane which may increase the time it takes the pressure to reach a fraction of the peak.

In some embodiments, the period of time it takes the pressure to return to the equilibrium pressure (pressure before applying the force) may indicate whether the membrane is blocked. In some embodiments, blockage of membrane 120 may be detected based on the amount of time it takes the pressure to equalize. In some embodiments, to determine when pressure equalizes, a pressure sensor may be used to measure pressure outside the sensing chamber. For example, if there is no blockage, the pressure equalizes in a short amount of time (almost instantaneously). In some embodiments, if the membrane is clogged less gas may be able to flow through the membrane which may increase the time it takes the pressure to equalize. In some embodiments, controller 160 may be configured to determine that membrane 120 is blocked responsive to the amount of time (to return to equilibrium or reach the fraction of the peak pressure) reaching a pre-determined time threshold (e.g., 50 microseconds).

In some embodiments, the rate of return, the amount of time to reach a fraction of the peak pressure, and/or the amount of time it takes the pressure to return to equilibrium pressure may further indicate an amount of membrane blockage. For example, the lower the rate of return the higher the membrane blockage. Similarly, the longer amount of time to reach a fraction of the peak pressure (or to return to equilibrium), the higher the membrane blockage.

In some embodiments, the larger the volume change, the longer the pressure takes to equalize in part due to larger pressure differential and higher volume of gas needing to escape the chamber. In some embodiments, the time it takes for the pressure to return to the relaxed state (or to reach the fraction of the pressure peak, or to equalize) "instantaneously" may also be dependent on the density of the gas. The larger the gas density, the longer it may take the pressure to equalize. This may be explained by the following equations:

Ideal Gas Law: $PV=nRT$

Where: P=Pressure, V=Volume, n=amount of material (generally either mass or mols), R=Gas Constant, T=Temperature Volumetric Flow Rate Equation: $Q=dv/dt=vA$ Where: Q=dv/dt=flow rate, v=velocity of fluid/flow, A=area fluid is flowing through.

Boyle's law: $P_1V_1=P_2V_2$

Where: P1=Pressure before volume change (atmospheric); P2=Pressure immediately after volume change; V1=Initial volume of sensing chamber, and V2=Volume of sensing chamber after volume change.

Dynamic Pressure Equation: $\Delta P = \dfrac{\rho v^2}{2}$

Where: $\Delta P=P2-P1$=Change in pressure; ρ=Fluid density; v=Velocity of fluid.

In some embodiments, the time it takes for the pressure to equalize "instantaneously" may be dependent on the porosity (permeability) of the membrane material. The lower the porosity, the longer it may take the pressure to equalize:

Volumetric Flowrate Equation: $Q = \dfrac{dV}{dt} = vA_{surf}$

Where: Q=dV/dt=Flowrate; v=velocity of fluid/flow; Asurf=Surface area where gas will flow (the pores in the membrane).

FIG. 1-A shows example charts illustrating the operation of a gas detector, in accordance with one or more embodiments. Charts 1-3 illustrate examples of relationships between the time it takes the pressure to equalize and different factors, according to one or more embodiments. For example, Chart 1 shows the relationship between the membrane porosity and time. Chart 2 shows the relationship between the volume change and time. Chart 3 shows the relationship between the fluid density and time.

Returning to FIG. 1, in some embodiments, a timer may be used for determining a time period it takes for the pressure inside the chamber to equalize. In some embodiments, the timer may be a stand-alone timer located inside the gas detector, may be included in controller 160, pressure sensor 150, or included in other components of gas detector 100. In some embodiments, the timer may be outside of gas detector 100. In some embodiments, the timer may be configured to start measuring time responsive to sensor 150 sensing a pressure change. In some embodiments, the timer may be configured to stop measuring time responsive to the pressure equalizing inside the chamber. In some embodiments, the timer may be configured to measure time periodically (e.g., based on a schedule), continuously (e.g., a clock), or on demand (from a user, controller, or components of gas detector 100).

In some embodiments, controller 160 may be configured to automatically activate the solenoid (by sending a current through the coil) to cause the volume change inside the sensing chamber. The controller 160 may activate the solenoid periodically to check (or test) for blockage in the membrane. For example, the controller may check for blockage on pre-determined schedule, on demand (e.g., locally, or remotely via a communication network), or based on previous test results. For example, if the period of time for equalizing or the amount of blockage determined during a previous test is outside of a defined range, the controller may check for blockage before the scheduled check. Similarly, if the period of time for equalizing or the amount of blockage determined during a previous test is within or below a defined range, the controller may skip a scheduled check for blockage.

In some embodiments, controller 160 may be configured to determine (or estimate) a remaining operational life of the membrane based on the determined amount of time or the determined amount of blockage of the membrane. For example, controller 160 may indicate whether or when the membrane should be cleaned or replaced based the determined amount of blockage or the determined amount of time it takes pressure to equalize.

In some embodiments, applying one or more forces to membrane 120 may cause the membrane to unclog (shake the debris off). For example, membrane 120 may become unclogged as a result of testing for blockage. In some embodiments, controller 160 may conduct a second test after a first test to check if membrane 120 is unclogged (or if there is change in the amount of blockage as a result of the first testing). In some embodiments, controller 160 may be configured to apply a stronger force to shake off debris responsive to determining that membrane 120 is clogged during a first test. The stronger force may be part of a second test, or may be intended for cleaning, in which case, controller 120 may run another test after applying the stronger force to check for changes in the amount of blockage.

In some embodiments, controller 160 may be configured to generate a feedback or alert including one or more of the amount of time it takes the pressure to equalize, a condition of the membrane, determination of whether the membrane is blocked, the amount of blockage, or an estimation of remaining operational life of the membrane. In some embodiments, the feedback may be displayed on a display of the gas detector. In some embodiments, controller 160 may generate an alarm (e.g., audible, or visual alarm) responsive to determining the condition of the membrane (e.g., lights, or alarm sounds). In some embodiments, different types of alarms may be used based on the condition of the membrane. For example, green light if the membrane is clean, yellow if it's blocked, red light it's torn or missing, etc. Similarly, different audible alarms (e.g., in volume, duration, intensity, etc.) may be based on the condition of the membrane. In some embodiments, the feedback/alert may be sent to a user device (e.g., via a communication network) which may allow users to remotely monitor operations of the gas detector (e.g., detecting the condition of the membrane). In some embodiments, controller 160 may be configured to communicate with a maintenance scheduling system to trigger a maintenance call based on the determined condition of the membrane. With this advance warning, the end-user may schedule maintenance to replace the membrane prior to failure and reduce costly down-time or gas detector failures due to blocked membranes.

In some embodiments, the current/voltage applied to effectuate the pressure change may be used to evaluate the actuator movement and thus interrogate the status of the membrane.

The above descriptions refer to time from peak pressure to a lower pressure. It should be obvious to anyone with average skill in the art that pressure variations in time between equilibrium (before pulse), actuated movement and peak pressure (observing rate of pressure increase) is as useful as looking at the pressure decay after peak pressure.

It is to be noted that the example of applying a force using a solenoid, shown in FIG. 1, is for illustrative purposes only and is not intended to be limiting. Different methods for applying a force on the membrane to cause volume change may be considered and are consistent with the present disclosure.

Figure 2:
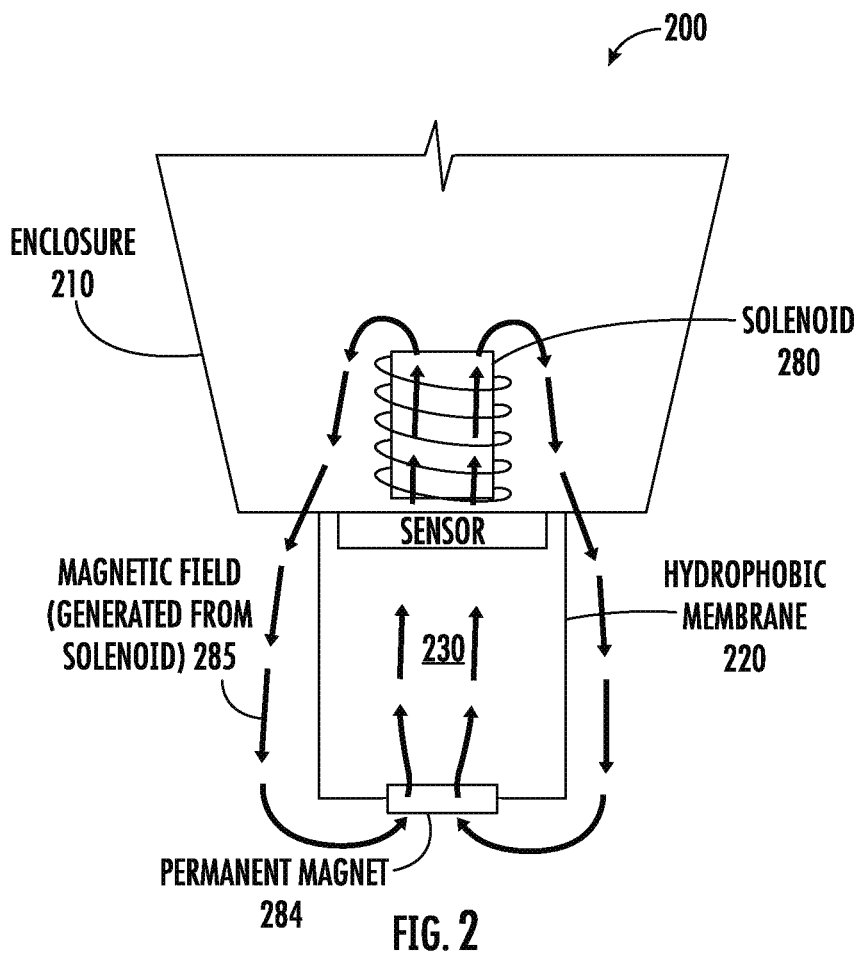
FIG. 2 is a perspective side view of an example of a gas detector, according to one or more embodiments.

For example, FIG. 2 shows a perspective side view of an example of a gas detector 200, according to one or more embodiments. Gas detector 200 may include an electromagnet 280 located anywhere within enclosure 210. Gas detector 200 may further include an actuator 284 operatively coupled to membrane 220 as well as to the electromagnet 280. In some embodiments, electromagnet 280 may be actuated (e.g., by a controller) to generate a magnetic field 285. The magnetic field may cause actuator 284 to move, thereby extending or compressing membrane 220 and changing the volume inside chamber 230. For example, actuator 284 may be pulled or pushed down by changing direction of the electric current which changes the polarity of the magnetic field of electromagnet 280. In some embodiments, locations of actuator 284 and electromagnet 280 may be interchanged. In some embodiments, actuator 284 may be permanent magnet an electromagnet, or an element of magnetic material (e.g., a magnetic element).

Figure 3:
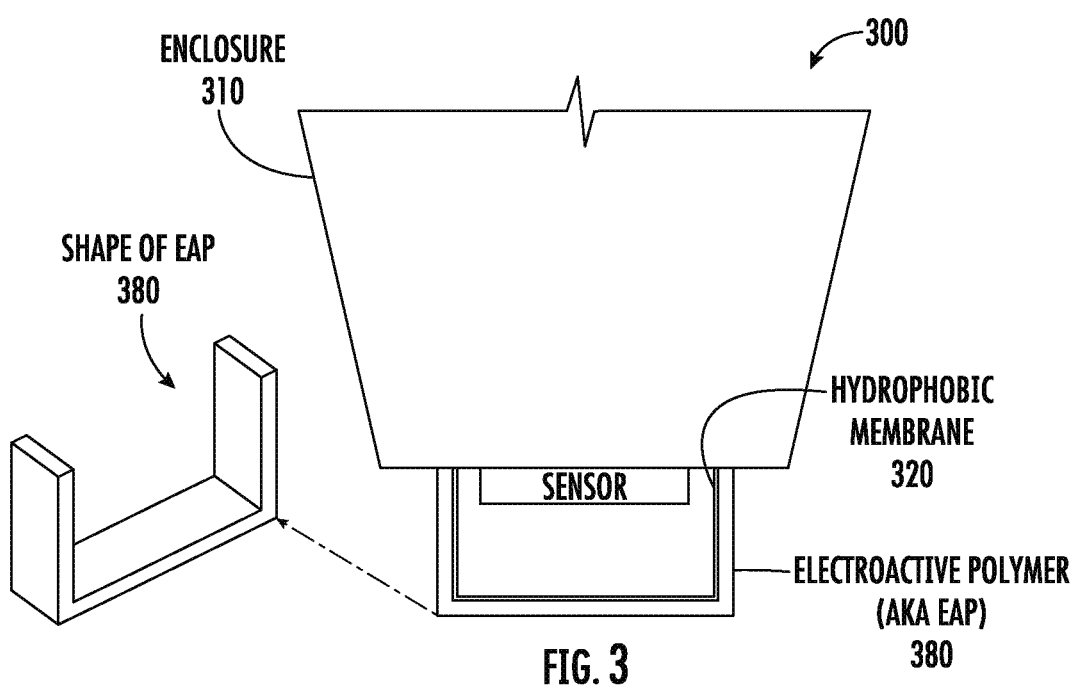
FIG. 3 is a perspective side view of an example of a gas detector with an electroactive polymer (EAP), according to one or more embodiments.

FIG. 3 illustrates a perspective side view of an example of a gas detector 300, according to one or more embodiments. In some embodiments, gas detector 300 may have an enclosure 310. Gas detector 300 may include an electroactive polymer (EAP) 380 operatively coupled to membrane 320. In some embodiments, electroactive polymer 380 may be located inside the sensing chamber or outside the sensing chamber. In some embodiments, electroactive polymer 380 may be coupled to one or more walls of membrane 320 (e.g., inner, or outer walls). In some embodiments, electroactive polymer 380 may be embedded in membrane 380. In some embodiments, electroactive polymer 380 may be configured to surround parts or of all of membrane 320. In some embodiments, as shown in FIG. 3, electroactive polymer 380 may be in a form a "shell" or "U" shape around parts of membrane 380. In some embodiments, an electric current may be applied to the electroactive polymer 380 causing it to flex and creating a force against membrane 320 which in turn changes the volume inside chamber 330 (e.g., increase or decrease).

In some embodiments, membrane 320 may be made out of an EAP. In some embodiments, membrane 320 may flex (when a current is applied to it) causing the volume inside the chamber to change.

In some embodiments, the gas detector may include a combination of an actuator and a moving body. The moving body may include a plurality of force inducing elements and may be operatively connected to the actuator and the membrane. In some embodiments, the combination of the actuator and moving body may be used to apply a force on the membrane and cause a volume change inside the sensing chamber. In some embodiments, the actuator may be configured to cause the moving body to move, which in response, applies a force on the membrane. In some embodiments, the actuator may be located within or outside the enclosure of the gas detector. In some embodiments, the actuator may be an electric actuator (e.g., electric motor), a magnetic actuator, a mechanical actuator, a pneumatic actuator, or other types of actuators. In some embodiments, the moving body may be located on or proximate to one or more walls of the membrane. In some embodiments, the moving body may be located outside or within the sensing chamber. For example, the moving body may be configured to apply the force from outside the membrane or from inside the membrane. In some embodiments, the plurality of force inducing elements of the moving body may optimize a geometric change in the membrane to cause the pressure change or to cause membrane cleaning (causing the membrane to vibrate or shake which in turn may cause debris/dirt to fall off).

In some embodiments, the moving body may be operatively connected to the controller. In these embodiments, the controller may act as the actuator. In some embodiments, the moving body may be one or more of an arm, a rod, a piston, a linkage, a button, or any other moving body configured to applying a force on the membrane and changing the volume inside the sensing chamber.

In some embodiments, a soft actuator configured for changing shape in response to an electric current, may be used to apply a force on the membrane (as a result of shape change of the actuator). In these embodiments, the soft actuator may act as the moving body. For example, the soft actuator may be operatively coupled with the membrane. In some embodiments, the soft actuator may be located on (or proximate) to one or more walls of the membrane (inner or outer walls). As explained above, a pressure sensor may measure the pressure change and a timer may measure the period of time to reach a preset fraction of the peak pressure inside the chamber. The measured time may indicate whether the membrane is blocked.

Figure 4:
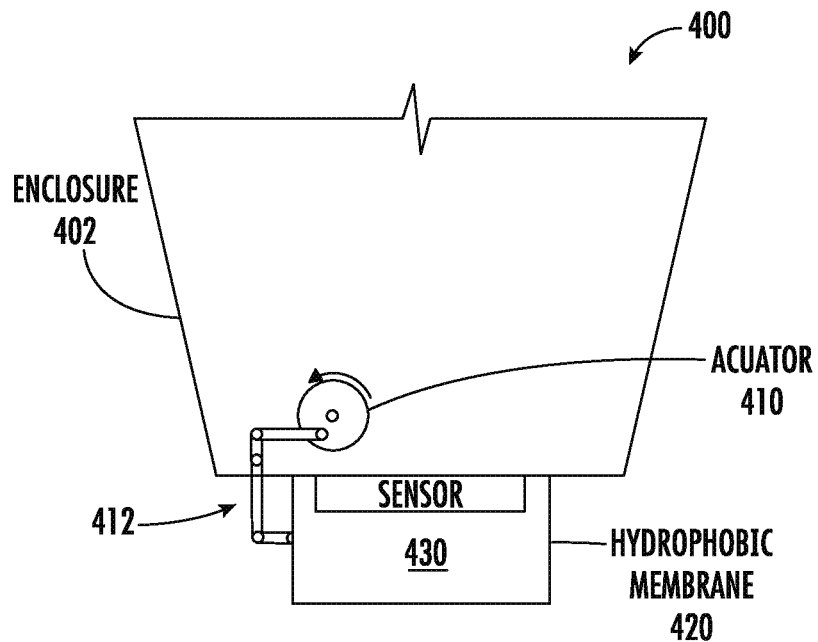
FIG. 4 is a perspective side view of an example of a gas detector with an actuator and a moving body, according to one or more embodiments.
Figure 5:
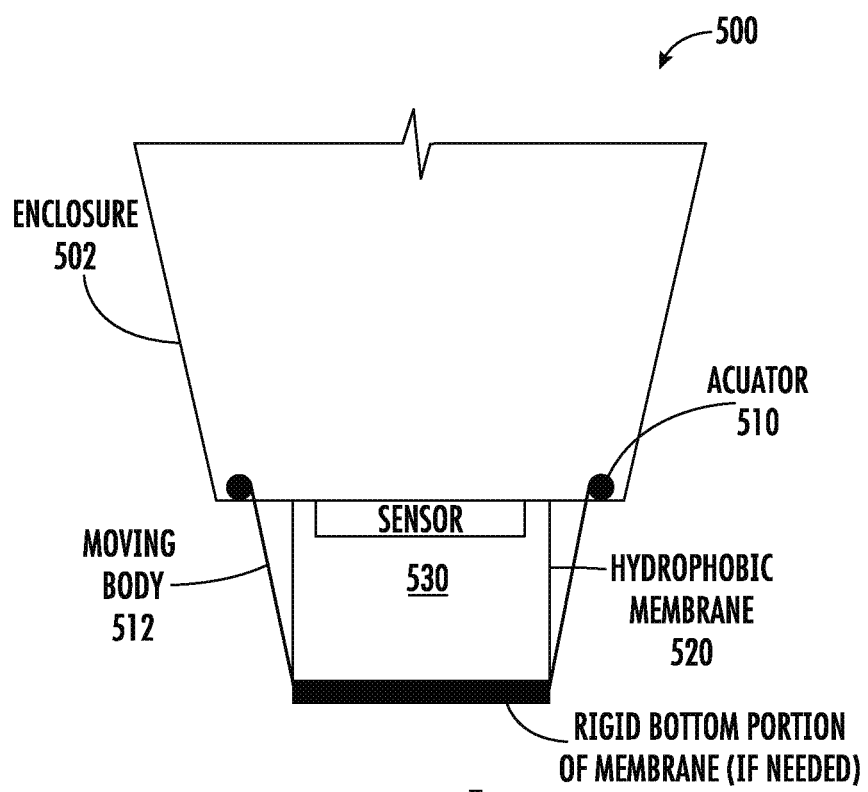
FIG. 5 is a perspective side view of an example of a gas detector with an actuator and a moving body, according to one or more embodiments.

FIGS. 4-5 illustrate examples of gas detectors including a combination of actuators and moving bodies, according to one or more embodiments. For example, FIG. 4, illustrates a perspective side view of an example of a gas detector 400 including an actuator 410 and a moving body 412, according to one or more embodiments. In this example, actuator 410 is a motor located within enclosure 402 of gas detector 400. Moving body 412 is a linkage. Moving body 412 is located outside sensing chamber 430. In this example, in response to the actuator 410 (motor) applying a force on one end of moving body 412 (linkage), the opposite end of the moving body applies a force on membrane 420 and creates a volume change inside sensing chamber 430. In some embodiments, actuator 410 may be an electric motor or a linear motor. In some embodiments, actuator 410 may be located inside or outside enclosure 402. In some embodiments, the moving body 412 may be a lever, arm, or a rod. In some embodiments, moving body 412 may be located inside sensing chamber 430 and configured to apply force on the inner walls of membrane 420.

FIG. 5, illustrates a perspective side view of gas detector 500 including an actuator 510 and a moving body 512, according to one or more or more embodiments. In this example, actuator 510 is a motor located within enclosure 502 of gas detector 500. Moving body 512 is a string or rope operatively connected with membrane 520 and actuator 510. In some embodiments, moving body 512 is configured to be moved by actuator 510 (e.g., pulled or pushed). In response, membrane 520 may be pulled or pushed up or down creating a volume change inside the sensing chamber 530. In some embodiments, membrane 512 may include a rigid portion 528 located in the bottom of the membrane to facilitate the pushing or pulling movement of the membrane. In some embodiments, a combination of a motor and string on each side of the membrane may be used.

It is to be noted that these examples are for illustrative purposes only and is not intended to be limiting. Other actuators and moving bodies for applying a force on the membrane to cause volume change may be considered and are consistent with the present disclosure.

Figure 6:
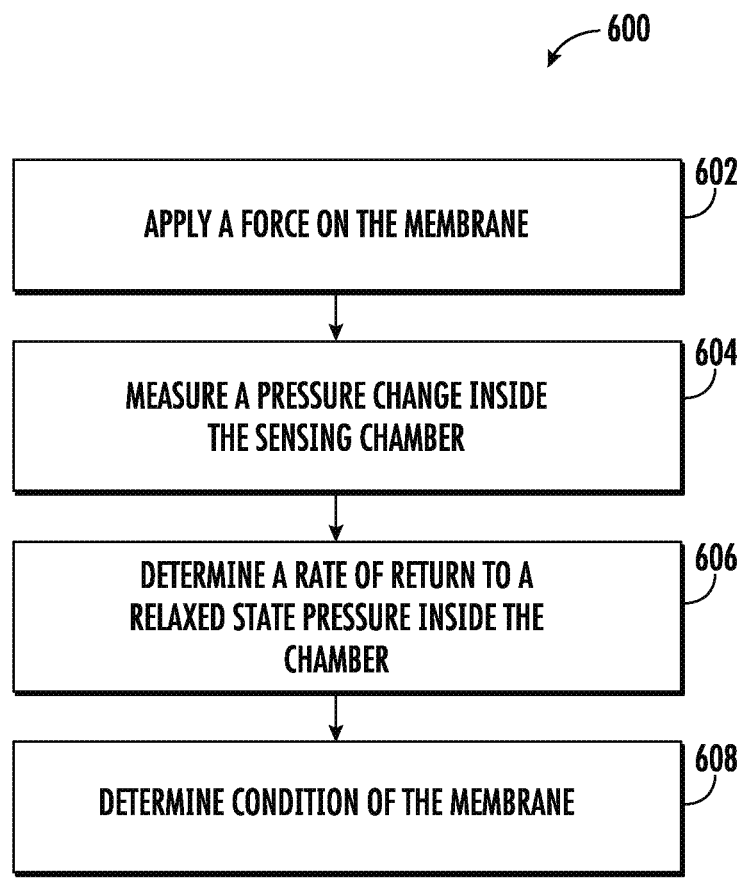
FIG. 6 shows a flow diagram illustrating an example of a method for detecting membrane blockage in a gas detector, in accordance with one or more embodiments.

FIG. 6 shows a flow diagram illustrating an example of a method 600 for detecting membrane blockage in a gas detector, in accordance with one or more embodiments of the present disclosure. In some embodiments, the gas detector comprises a membrane defining a sensing chamber of the detector, the sensing chamber comprising a relaxed state pressure.

At an operation 602 of method 600, a force may be applied on one or more walls of the membrane. Applying the force may cause a volume change inside the sensing chamber. In some embodiments, operation 602 may be performed by a controller the same as or similar to controller 160 (shown in FIG. 1 and described herein).

At an operation 604 of method 600, a pressure change inside the sensing chamber caused by the volume change may be measured. In some embodiments, operation 604 may be performed by a pressure sensor the same as or similar to pressure sensor 150 (shown in FIG. 1 and described herein).

At an operation 606 of method 600, a rate of return to the relaxed state pressure inside the chamber may be determined. In some embodiments, operation 606 may be performed by controller the same as or similar to controller 160 (shown in FIG. 1 and described herein).

At an operation 608 of method 600, a condition of the membrane may be determined based on the determined rate of return to the relaxed state pressure. In some embodiments, operation 608 may be performed by controller the same as or similar to controller 160 (shown in FIG. 1 and described herein).

It should be understood that the description and the drawings are not intended to limit the invention to the particular form disclosed, but to the contrary, the intention is to cover all modifications, equivalents, and alternatives falling within the spirit and scope of the present invention as defined by the appended claims. Further modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every.

What is claimed is:

1. A method for detecting membrane blockage in a gas detector comprising a membrane defining a sensing chamber of the detector, the sensing chamber comprising a relaxed state pressure, the method comprising:
    applying one or more forces on one or more walls of the membrane, wherein applying the force causes a volume change inside the sensing chamber;
    measuring a pressure change inside the sensing chamber, the pressure change being caused by the volume change;
    determining a rate of return to the relaxed state pressure inside the chamber; and
    determining a condition of the membrane based on the determined rate of return to the relaxed state pressure.

2. The method of claim 1, wherein determining the rate of return to the relaxed state pressure comprises determining an amount of time for the pressure inside the chamber to reach a fraction of a peak pressure change.

3. The method of claim 1, wherein the determined condition indicates presence of blockage in the membrane.

4. The method of claim 1, wherein the determined condition indicates whether the membrane is ruptured or missing.

5. The method of claim 3, wherein presence of blockage in the membrane is determined responsive to the determined rate of return being above a threshold rate of return.

6. The method of claim 5, wherein the threshold rate of return is determined based on at least one of: porosity of the membrane, an amount of volume change, and type of gas inside the sensing chamber.

7. The method of claim 1, further comprising:
determining an amount of blockage of the membrane based on the determined rate of return.

8. The method of claim 1, further comprising:
determining a remaining operational life of the membrane based on the determined rate of return.

9. The method of claim 1, further comprising:
sending an alert to a user, the alert indicating the condition of the membrane.

10. The method of claim 1, wherein the one or more forces cause debris to fall off the membrane.

11. A gas detector comprising:
a membrane configured to define a sensing chamber of the gas detector, the sensing chamber comprising a relaxed state pressure;
a moving body operatively connected to one or more walls of the membrane, the moving body configured to apply one or more or more forces on the one or more walls of the membrane, wherein applying the force causes a volume change inside the sensing chamber;
a pressure sensor configured for measuring pressure change inside the sensing chamber, the pressure change being caused by the volume change; and
a controller operatively connected to the pressure sensor and the moving body, the controller configured to:
determine a rate of return to the relaxed state pressure inside the chamber; and
determine a condition of the membrane based on the determined rate of return to the relaxed state pressure.

12. The system of claim 11, wherein determining the rate of return to the relaxed state pressure comprises determining an amount of time for the pressure inside the chamber to reach a fraction of a peak pressure change.

13. The gas detector of claim 11, wherein the determined condition indicates presence of blockage in the membrane.

14. The gas detector of claim 13, wherein presence of blockage in the membrane is determined responsive to the determined rate of return being above a threshold rate of return.

15. The gas detector of claim 14, wherein the threshold rate of return is determined based on at least one of: porosity of the membrane, an amount of volume change, and type of gas inside the sensing chamber.

16. The gas detector of claim 13, wherein the controller is further configured to:
determine an amount of blockage of the membrane based on the determined rate of return.

17. The gas detector of claim 16, wherein the controller is further configured to:
determine a remaining operational life of the membrane based on the determined amount of blockage of the membrane.

18. The gas detector of claim 11, wherein the moving body is an electroactive polymer.

19. The gas detector of claim 18, wherein the electroactive polymer is embedded in the membrane.

20. The gas detector of claim 11, further comprising:
an actuator operatively coupled with the moving body and the controller, the actuator configured to cause the moving body to apply the force on the membrane.

* * * * *